US011020235B2

(12) United States Patent
Seifert et al.

(10) Patent No.: US 11,020,235 B2
(45) Date of Patent: Jun. 1, 2021

(54) SYSTEM AND METHOD FOR INSTALLING AN ANNULAR REPAIR RIVET THROUGH A VERTEBRAL BODY PORT

(71) Applicant: GLOBUS MEDICAL, INC., Audubon, PA (US)

(72) Inventors: Jody Seifert, Birdsboro, PA (US); Sean Suh, Morganville, NJ (US); Mark Weiman, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 140 days.

(21) Appl. No.: 15/493,794

(22) Filed: Apr. 21, 2017

(65) Prior Publication Data

US 2017/0224501 A1 Aug. 10, 2017

Related U.S. Application Data

(63) Continuation of application No. 14/280,185, filed on May 16, 2014, now Pat. No. 9,655,736, which is a continuation of application No. 13/591,961, filed on Aug. 22, 2012, now Pat. No. 8,758,440, which is a continuation of application No. 12/564,525, filed on Sep. 22, 2009, now Pat. No. 8,273,110.

(51) Int. Cl.
A61F 2/44 (2006.01)
A61F 2/46 (2006.01)
A61F 2/30 (2006.01)

(52) U.S. Cl.
CPC ............ *A61F 2/442* (2013.01); *A61F 2/4611* (2013.01); *A61F 2002/30359* (2013.01); *A61F 2002/30405* (2013.01); *A61F 2002/30522* (2013.01); *A61F 2002/30604* (2013.01); *A61F 2002/4435* (2013.01)

(58) Field of Classification Search
CPC .......................... A61F 2/442; A61F 2002/4435
See application file for complete search history.

(56) References Cited

U.S. PATENT DOCUMENTS

2004/0002764 A1* 1/2004 Gainor ............... A61B 17/0057
623/17.16
2007/0179527 A1* 8/2007 Eskuri ................ A61B 17/0057
606/213

\* cited by examiner

*Primary Examiner* — Olivia C Chang

(57) ABSTRACT

A two part annulus repair rivet for repairing a defect in the annulus of an intervertebral disc includes a first part delivered through a port and adapted to be positioned at an internal surface of an annulus adjacent a defect and a second part adapted to be positioned on an external surface of the annulus adjacent the defect. The first and second parts are secured together, repairing the defect.

18 Claims, 5 Drawing Sheets

SYSTEM AND METHOD FOR INSTALLING AN ANNULAR REPAIR RIVET THROUGH A VERTEBRAL BODY PORT

CROSS REFERENCE TO RELATED APPLICATIONS

The present application is a Continuation of U.S. patent application Ser. No. 14/280,185 filed on May 16, 2014, which is a Continuation of U.S. patent application Ser. No. 13/591,961 filed on Aug. 22, 2012, now allowed, which is a Continuation of U.S. patent application Ser. No. 12/564,525 filed on Sep. 22, 2009, which issued as U.S. Pat. No. 8,273,110. The content and subject matter of these applications are hereby incorporated by reference in their entirety, including all text and figures, for all purposes.

FIELD OF THE INVENTION

The present invention relates to minimally invasive spinal surgery.

BACKGROUND OF THE INVENTION

The annulus of intervertebral discs develop defects or tears, and a portion of the nucleus pulposus can be squeezed toward, into or through the defect or tear. This creates pain and discomfort. Methods have been developed to repair these tears in the annulus. These methods include using sutures to close the tear. The sutures, however, can fail over time. Other methods use plugs that are inserted into the tear. These plugs, however, are typically inserted from the exterior of the annulus and require difficult positioning or enlarging of the tear to accommodate insertion of the plug. Some plugs only cover the external side of the annulus tear.

Therefore, systems and methods are desired for annulus repair that cover both the internal and external surfaces of the annulus and that provide for access to the internal surface of the annulus for improved attachment of a repair device to the annulus.

SUMMARY OF THE INVENTION

Exemplary embodiments of the present invention are directed to a method and system for repairing tears or ruptures in an annulus. Access is provided to the center or nucleus pulposus of an intervertebral disc through a port in either one of the vertebrae that are adjacent that intervertebral disc. Therefore, access to the interior of the disc is provided without cutting or otherwise further disrupting the integrity of the annulus, maintaining the current status of the annulus. Access through a given vertebra is provided anywhere around the vertebral body surface, for example, anterior, lateral, pedicular, A/P, transfacet and end plates. The port terminates at any point inside the annulus.

The port in the vertebra facilitates a bi-directional approach to repairing tears or defects in the intervertebral disc annulus. In this bi-directional approach, two mating rivets are used to repair the tear in the annulus. One rivet accesses the tear from the exterior surface of the annulus, and the other rivet accesses the tear from the interior surface of the annulus through the port in the vertebra. Each rivet includes a flange or wings that are shaped with controlled height that limits the range of bend motion in the spine. In addition, the wings are wide enough to act as a barrier between the nucleus and the annulus tear.

In accordance with one exemplary embodiment, the present invention is directed to a method for annulus repair where a port is established through a vertebral body and vertebral endplate and into a nucleus of an intervertebral disc with an annulus having a tear. The port is created by drilling a cylindrical shaft through the vertebral body that intersects the vertebral endplate at an angle less than 90° and greater than 0°. The shaft enters an exterior surface of the vertebral body opposite the tear.

An internal rivet tool is releasably attached to a distal end of a first part of a two-part annulus repair rivet. The distal end is larger than the port, and the internal rivet tool is used to push the first part through the port, deforming the distal end. The proximal portion of the first part that extends from the distal end is inserted through the tear in the annulus until the distal end contacts an interior surface of the annulus. A separate external rivet tool that is releasably attached to a distal end of the second part of the annulus repair rivet positions a proximal portion of the second part that extends from the distal end in contact with the proximal portion of the first part of the annulus repair rivet.

In one embodiment, each proximal portion is one part of a two-part mechanical fastener. The first part of the two-part mechanical fastener is a socket containing a plurality of concentric collars, and the second part of the two-part mechanical fastener is a stem having a plurality of barbs. The first part and second parts of the annulus repair rivet are secured together by pushing on both the internal and external rivet tools to insert the stem in the socket such that barbs on the stem engage collars in the socket. The internal and external rivet tools are released from their respective distal ends of annulus repair rivet, and the internal rivet tool is removed from the port.

In one embodiment, each annulus repair rivet has a distal end and a proximal portion extending from the distal end. Each distal end has an area sufficient to completely cover the tear and a height equal to a height of the annulus. In addition, each distal end is formed with a curvature complementing a curvature of the annulus to provide a form-fitting mating between each distal end and the annulus. In addition, the proximal portion of the first part of the annulus repair rivet has a length equal to a wall thickness of the annulus, and the proximal portion of the second part of the annulus repair rivet has a length greater than wall thickness of the annulus. In one embodiment, the port in the vertebra is a cylindrical shaft through the vertebral body, and at least one of a height or a width of the distal end of the first part of the annulus repair rivet exceeds a diameter of the port.

DETAILED DESCRIPTION

Figure 1:
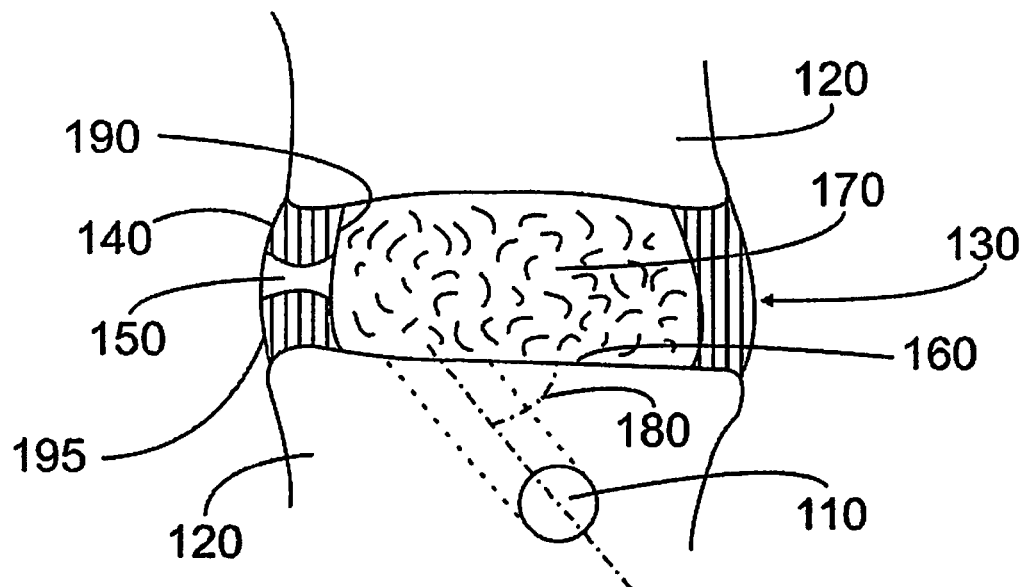
FIG. 1 is a representation of an embodiment of a port drilled through a vertebra into an intervertebral disc to repair a tear in an annulus in accordance with the present invention.

Referring initially to FIG. 1, a port 110 is established through one of the vertebral bodies 120 adjacent the intervertebral disc 130 having an annulus 140 with a tear or defect 150 that is to be repaired. Although illustrated in the inferior vertebra, the port 110 can also be located in the superior vertebra. Suitable methods for forming the port are known and available to one of skill in the art and include drilling. In one embodiment, the port 110 is a cylindrical shaft having a circular cross section. However, the port can have other cross-sectional shapes, for example, a rectangular cross section.

The port extends through the vertebral endplate 160 and into a nucleus 170 of the intervertebral disc. In general, the port is formed as a shaft that angled with respect to the endplate of the vertebral body. In one embodiment, the shaft passes through the vertebral body 120 and intersects the vertebral endplate 160 at an angle 180 less than about 90° and greater than about 0°. In another embodiment, the shaft intersects the vertebral endplate at an angle of form about 30° to about 45°. Suitable methods for creating the port are known and available to one of skill in the art and include drilling.

The shaft is positioned to provide direct or straight line access to the defect or tear on the interior surface of the annulus. In one embodiment, the shaft enters the exterior surface of the vertebral body opposite the defect or tear. Therefore, a straight rod can be used to push an annulus repair rivet through the shaft and into contact with the interior surface of the annulus.

Figure 2:
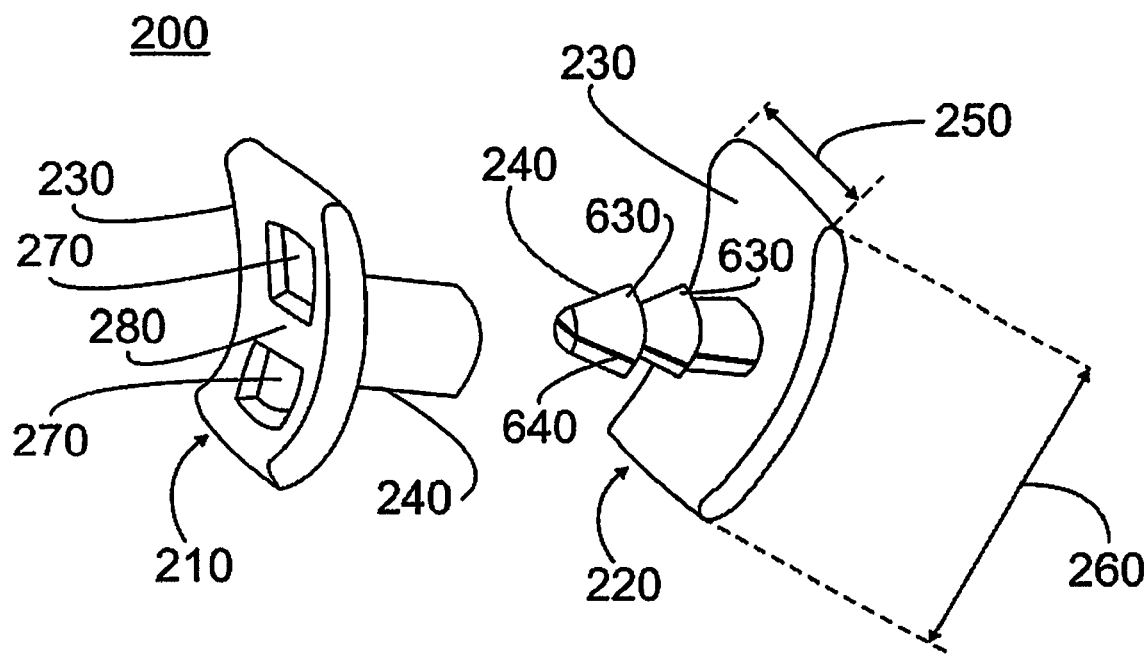
FIG. 2 is a representation of an embodiment of a two-part annulus repair rivet for use in accordance with the present invention.

The port is used to facilitate a bi-directional, i.e., internal and external, approach to repairing tears or defects in the annulus using a two-part annulus repair rivet. An exemplary embodiment of a two-part annulus repair rivet 200 for use with the present invention is illustrated in FIG. 2. The annulus repair rivet includes a first or internal part 210 that is brought into contact with an internal surface 190 (FIG. 1) of the annulus through the port and a second or external part 220 that is brought into contact with an external surface 195 (FIG. 1) of the annulus. Suitable materials for the annulus repair rivet are rigid enough to close the annulus defect or tear and to provide a desired amount of cushioning between, adjacent vertebrae and flexible enough to be deformed when passed through the port. These materials include, but are not limited to, elastomers. The first and second parts can be constructed of the same material or different materials.

In one embodiment, each annulus repair rivet includes a distal end 230 and a proximal portion 240 extending from the distal end 230. Each distal end has a size or area sufficient to completely cover the annulus defect or tear 150. Although each distal end 230 could be any shape, for example circular or oval, preferably, each distal end is generally rectangular in shape, having a height 260 and a width 250. In one embodiment, each distal end has a height 260 equal to a height of the annulus 140 as measured between adjacent vertebrae. Therefore, the distal ends span the entire sides of both the interior and exterior of the annulus adjacent the defect or tear, providing for maximum coverage of the defect or tear in the height direction. In addition, the distal ends, being made of an elastomeric material that is deformable, provide cushioning between adjacent vertebrae and control or limit the range of motion between these vertebrae.

When the first and second parts of the annulus repair rivet are brought into contact with the interior and exterior surfaces of the annulus respectively, the distal ends completely cover the annulus defect or tear. In addition, the distal ends are shaped or curved to provide a form-fitting arrangement between the annulus and the annulus repair rivet. This eliminates gaps that could allow the nucleus to emerge past the annulus repair rivet. In one embodiment, each distal end has a curvature the complements the curvature of the annulus to provide a form-fitting mating between each distal end and the annulus. As is shown in FIG. 2, the first and second parts of the annulus repair rivet have opposite curvatures with regard to the proximal portion. For the first part of the annulus repair rivet 210, the proximal end 240 extends from a convex side of the curved distal end 230. For the second part of the annulus repair rivet 220, the distal end 240 extends from a concave side of the curved distal end 230. Therefore, the first part will mate with the interior surface of the annulus when the proximal portion extends through the defect or tear, and the second part will mate with the exterior surface of the annulus when the proximal portion extends through the defect or tear.

The proximal portions of the annulus repair rivets of the first and second parts contact each other through the annulus defect or tear and are used to secure the two parts together and to hold the annulus repair rivet to the annulus. In one embodiment, each proximal portion includes or is configured as one part of a two-part mechanical fastener. Therefore, securing the first part of the annulus repair rivet to the second part of the annulus repair rivet involves engaging the first part of the two-part mechanical fastener in the second part of the two-part mechanical fastener. Suitable two-part mechanical fasteners include, but are not limited to, mating male and female threaded fittings.

Figure 6:
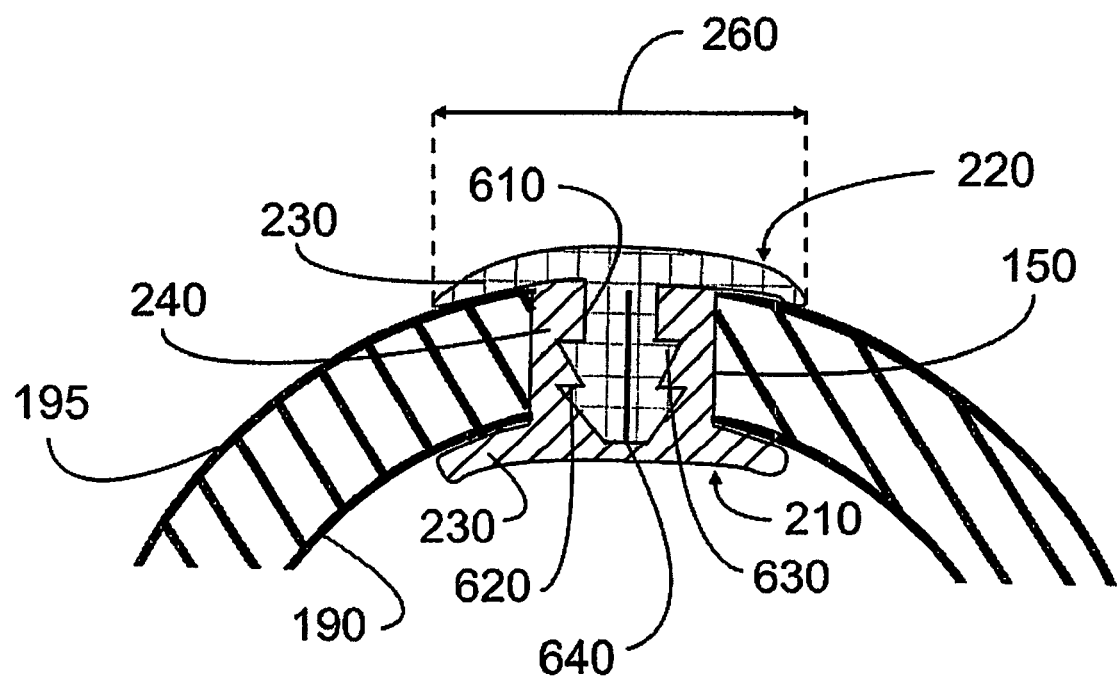
FIG. 6 is a representation illustrating a partial cross section of the intervertebral disc with the annulus repair rivet secured to the annulus.

According to one variation, the two-part mechanical fastener allows the two parts of the annulus repair rivet to be pressed together and secured. Referring to FIGS. 2 and 6, in one embodiment the proximal portion 240 of the first part 210 of the two-part mechanical fastener is a female fitting or socket 610 having a cylindrical shaft and including a plurality of concentric collars 620 extending into the cylindrical shaft and spaced along its length. The proximal portion 240 of the second part 220 of the two-part mechanical fastener is a male fitting or stem having a plurality of wedge-shaped barbs 630. Each barb extends around the outer circumference of the proximal portion, and the plurality of barbs is spaced along the length of the proximal portion. Although illustrated with two barbs and two collars, the number of barbs and collars can be varied. For example, a larger number of barbs and collars provides for a finer degree of fit between the annulus repair rivet and the thickness of the annulus.

In order to secure the first part of the annulus repair rivet to the second part, the stem is inserted into the socket such that the barbs engage the collars. The proximal portion 240 of the first part 210 has a length extending from the distal end 230 that is substantially equal to the wall thickness of the annulus. Therefore, when the first and second parts are pushed together, the proximal portion of the first part does not extend through the defect or tear past the exterior surface of the annulus. The proximal portion 240 of the second part 220 has a length extending from the distal end 230 that is longer than the wall thickness of the annulus. Therefore, when the first and second parts are pushed together, the proximal portion of the second part extends into the distal end of the first part. In one embodiment, the proximal portion of the second part extends completely through the distal end of the first part, facilitating removal or disengagement of the stem from the socket. In one variation, the proximal portions 240 extend generally orthogonal to the distal ends, although they may be angled to accommodate the insertion trajectory or angle of the port, for example.

In one embodiment, the stem can also include a central slot 640. This allows the stem to deform when being inserted into or removed from the socket 610. In addition, each distal end can have one or more grooves 270 and ridges 280 (FIG. 2) on a surface opposite the surface that contacts the annulus. These grooves and ridges provide points of attachment or grips for tools used to attached the annulus repair rivet to the annulus.

Figure 3:
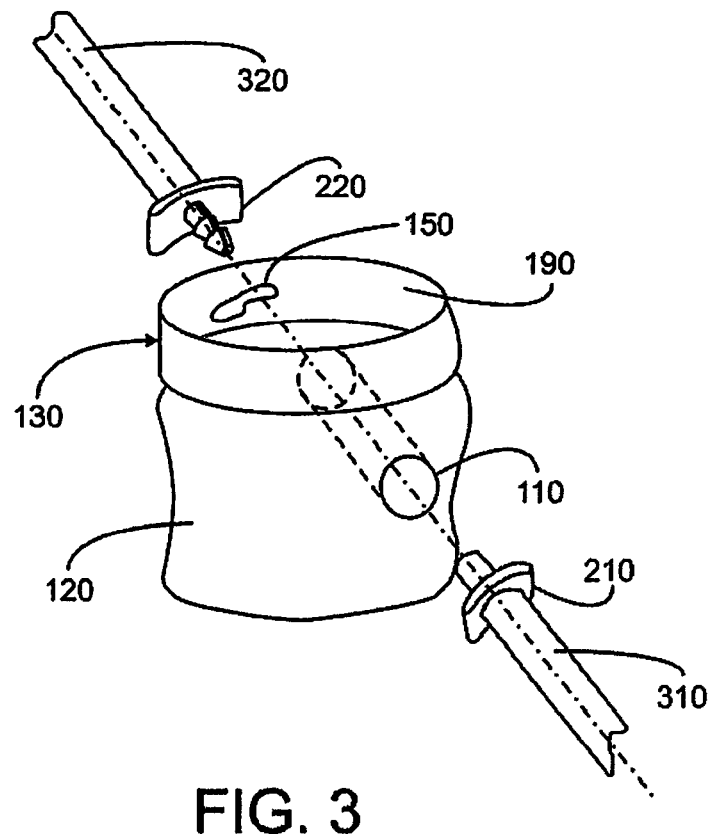
FIG. 3 is a representation illustrating a perspective view of an embodiment of the attachment of the annulus repair rivet to the annulus tear.

Referring to FIG. 3, after the port 110 is created in the vertebral body 120 from a point opposite the defect or tear 150 through the vertebral endplate and into the interior of the intervertebral disc 130, an internal rivet tool 310 is releasably attached to the first part 210 of the two-part annulus repair rivet, and a separate external rivet tool 320 is releasably attached to the second part 220 of the two-part annulus repair rivet. The rivet tools grip the grooves and ridges on the distal end of the first and second parts. In one embodiment, both the internal and external rivet tools are rigid cylindrical rods that can push the two parts the annulus repair rivet together.

The internal rivet tool 310 has a diameter small enough to pass through the shaft and a length long enough to extend completely through the port and to position the first part of the annulus repair rivet at an internal surface 190 of the annulus adjacent the defect or tear 150. Since the port 110 is a cylindrical shaft through the vertebral body and at least one of the height 250 or a width 260 of the distal end of the first part 210 of the annulus repair rivet can exceed the diameter of the port, the internal rivet tool passes the first part of the two-part annulus repair rivet through the port by pushing the first part through the port and deforming the larger distal end. The distal end reforms when it emerges in the space internal to the annulus. The internal rivet tool inserts the proximal portion of the first part that extends from the distal end through the defect or tear in the annulus until the distal end contacts an interior surface of the annulus.

The external rivet tool 320 positions the second part of the two-part annulus repair rivet at an external surface of the annulus adjacent the defect or tear. Therefore, the proximal portion of the second part is in contact with the proximal portion of the first part of the annulus repair rivet.

Figure 4:
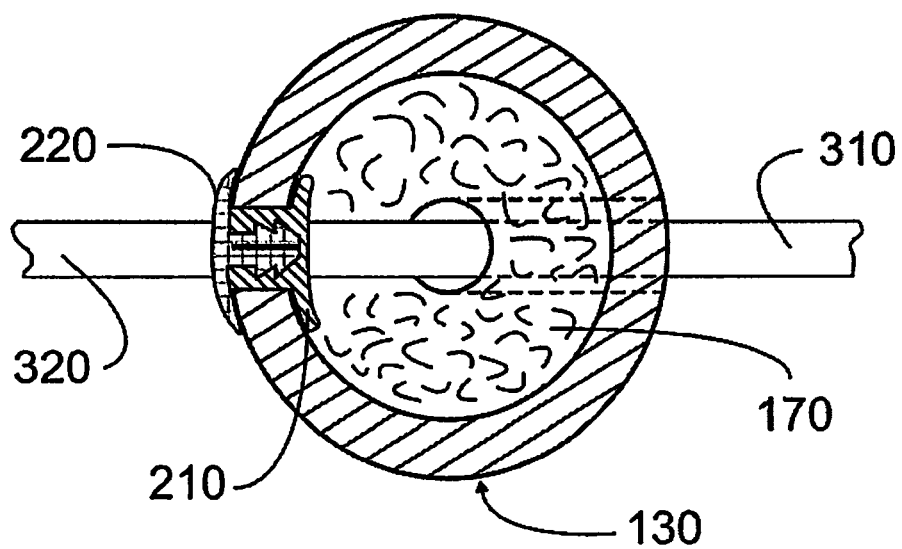
FIG. 4 is a representation illustrating a cross section of the intervertebral disc with the annulus repair rivet secured to the annulus.
Figure 5A:
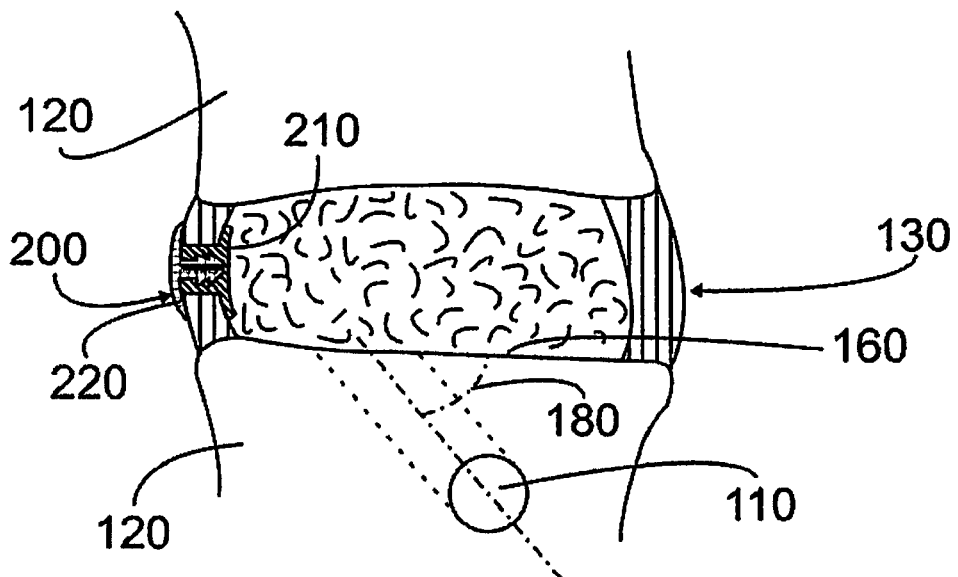
FIGS. 5A-5B are representations illustrating the annulus repair rivet secured to the annulus in a neutral state and under deflection of the vertebrae, respectively.
Figure 5B:
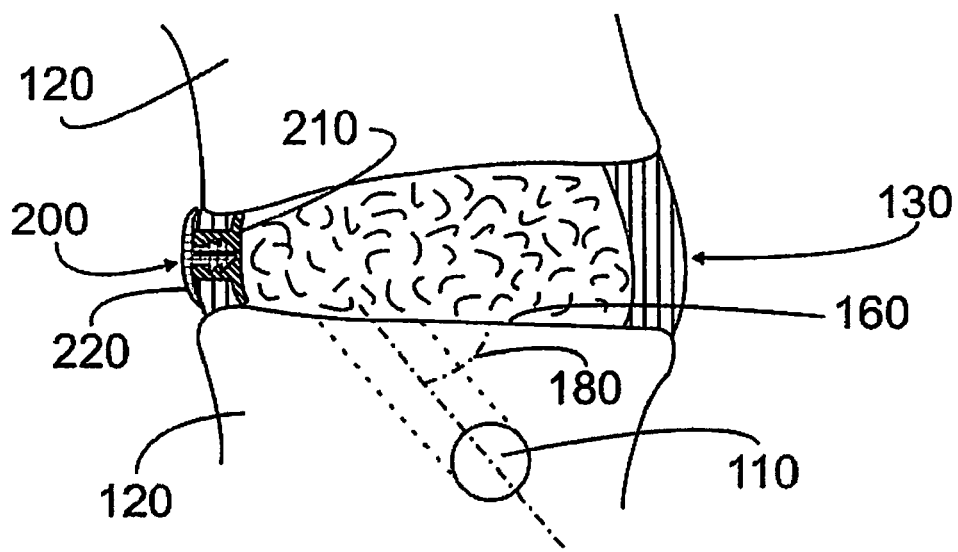

Referring to FIG. 4, the first part 210 of the annulus repair rivet is secured to the second part 220 of the annulus repair rivet to close the defect or tear in the annulus. Securing is accomplished by pushing on both the internal and external rivet tools to insert the stem in the socket such that the barbs engage the collars. The internal and external rivet tools are then released from the respective distal ends of the annulus repair rivets, and the internal rivet tool is removed from the port. As illustrated in FIG. 5, the annulus repair rivet 200 is attached to the annulus, sealing the annulus defect or tear. The distal ends of the first and second parts can deform under the relative motion between the adjacent vertebrae, providing cushioning and controlling the range of motion. The port 110 is sealed using methods known and available to one of skill in the art.

Figure 7:
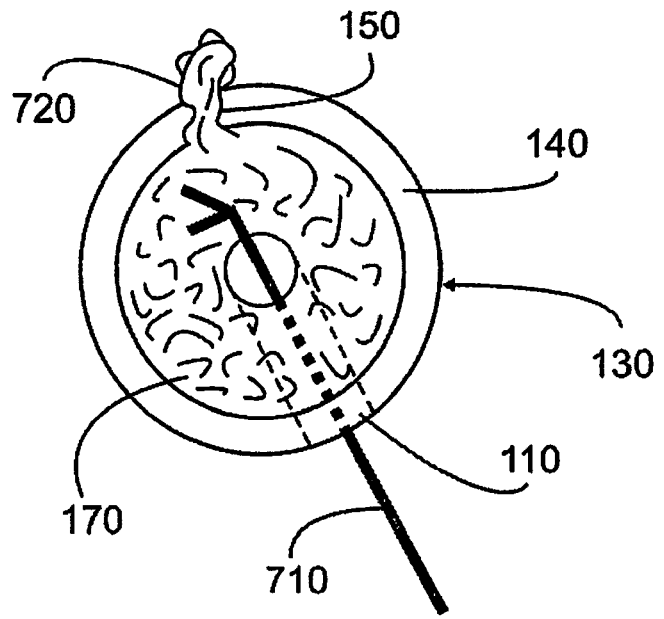
FIG. 7 is a representation illustrating a cross section of the intervertebral disc with a portion of the nucleus pulposus extending through the annulus tear and a tool inserted through a port in the vertebra.
Figure 8:
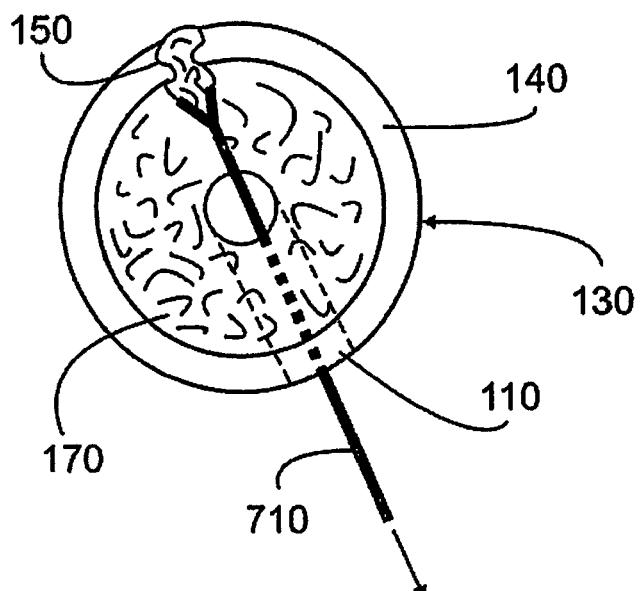
FIG. 8 is a representation illustrating a partial cross section of the intervertebral disc with a tool pulling a portion of the nucleus pulposus back through the annulus tear.

Referring to FIG. 7, a portion 720 of the nucleus pulposus 170 may have emerged from the intervertebral disc 130 through the defect or tear 150 in the annulus 140. Therefore, this portion 720 may be removed from the defect or tear before the two-part annulus repair rivet is used to repair the defect or tear. In one embodiment, after the port 110 is created in the vertebra, a tool 710 is inserted through the port 110, into the nucleus pulposus 170. The tool is sized to fit through the port and to grip the emerging portion 720 of the nucleus pulposus. One of such suitable tools may include forceps. The tool 710 is extended through the defect or tear 150 to grip the emerging portion 720 and to pull that portion back through the defect or tear 150 to the interior of the disc as illustrated in FIG. 8. The tool is removed, and the annulus repair rivet can then be attached as described herein. It may also be necessary to remove a portion of the nucleus pulposus through the port 110 to facilitate insertion of the first part of the two-part annulus repair rivet. In another embodiment, such a tool may be used with a healthy annulus and/or independent of the annulus to remove a defective nucleus as desired. In this regard, the aforementioned method may be used to access and remove the nucleus without breaching the annulus whatsoever, thereby maintaining the integrity of the annulus. Further, an artificial nucleus material may be inserted through the same access port.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A two part annulus repair rivet system comprising:
   a first rivet tool;
   a second rivet tool;
   a first part configured to be delivered through a port via the first rivet tool and adapted to be positioned at an internal surface of an annulus adjacent a defect, the first part having a curved distal end and a proximal portion extending from a convex side of the distal end;
   a second part adapted to be positioned on an external surface of the annulus adjacent the defect via the second rivet tool separate from the first rivet tool, the second part having a curved distal end and a proximal portion extending from a concave side of the distal end;
   wherein the proximal portion of the first part includes a female socket having an opening, the opening extending partially into the first part and configured to receive and engage the proximal portion of the second part to close the defect in the annulus,
   wherein the proximal portion of the second part includes a plurality of barbs that extend around the circumference of the proximal portion.

2. The two annulus repair rivet system of claim 1, wherein the proximal portion of the second part comprises a male fitting configured to be received within the female socket of the first part.

3. The two part annulus repair rivet system of claim 1, wherein the female socket comprises a cylindrical shaft.

4. The two part annulus repair rivet system of claim 3, wherein the socket contains a plurality of concentric collars.

5. The two part annulus repair rivet system of claim 4, wherein the proximal portion of the second part comprises a stem, wherein the stem is inserted in the socket such that the plurality of barbs engage the collars.

6. The two part annulus repair rivet system of claim 5, wherein the stem includes a central slot configured to allow the stem to deform when being inserted into or removed from the socket.

7. The two part annulus repair rivet system of claim 1, wherein the proximal portion of the first part has a length extending from the distal end that is substantially equal to a wall thickness of the annulus.

8. The two part annulus repair rivet system of claim 7, wherein the proximal portion of the second part has a length extending from the distal end that is longer than the wall thickness of the annulus.

9. The two part annulus repair rivet system of claim 1, wherein the distal end of the first part includes one or more grooves and ridges on a surface opposite to the convex side.

10. The two part annulus repair rivet system of claim 1, wherein the convex side of the first part is configured to mate with the internal surface of the annulus and the concave side of the second part is configured to mate with the external surface of the annulus.

11. The two part annulus repair rivet system of claim 1, wherein the distal end of the first part and the distal end of the second part each have an area sufficient to completely cover the defect.

12. The two part annulus repair rivet system of claim 1, wherein the first rivet tool is configured to engage the first part from the convex side of the distal end of the first part and the second rivet tool is configured to engage the second part from the concave side of the distal end of the second part.

13. A two part annulus repair rivet system comprising:
a pair of rivet tools;
a first part having a distal end and a proximal portion, the distal end being curved and having a convex side and a concave side, the proximal portion extending from the convex side of the distal end, wherein the first part is configured to be delivered through a port and is adapted to be positioned at an internal surface of an annulus adjacent a defect;
a second part having a distal end and a proximal portion, the distal end being curved and having a convex side and a concave side, the proximal portion extending from the concave side of the distal end, wherein the second part is configured to be delivered separately and is adapted to be positioned on an external surface of the annulus adjacent the defect;
wherein the proximal portion of the first part includes a female socket having an opening, the opening extending partially into the first part and configured to receive and engage the proximal portion of the second part to close the defect in the annulus,
wherein the proximal portion of the second part includes a plurality of barbs that extend around the circumference of the proximal portion, and
wherein the first part is configured to be secured to the second part using the pair of rivet tools.

14. The two part annulus repair rivet system of claim 13, wherein the convex side of the first part is configured to mate with the internal surface of the annulus and the concave side of the first part is configured to retain the nucleus pulposus.

15. The two part annulus repair rivet system of claim 13, wherein the concave side of the second part is configured to mate with the external surface of the annulus and the convex side of the second part is configured to cover a portion of the annulus.

16. The two part annulus repair rivet system of claim 13, wherein the first part is configured to be delivered through the port with one of the pair of rivet tools to position the first part at the internal surface of the annulus adjacent the defect.

17. The two part annulus repair rivet system of claim 16, wherein the second part is configured to be delivered with the other of the pair of rivet tools to position the second part at the external surface of the annulus adjacent the defect.

18. The two part annulus repair rivet system of claim 13, wherein one of the pair of rivet tools is configured to engage the first part from the convex side of the distal end of the first part and the other of the pair of rivet tools is configured to engage the second part from the concave side of the distal end of the second part.

* * * * *